United States Patent
Rajendran et al.

(10) Patent No.: US 10,196,371 B2
(45) Date of Patent: Feb. 5, 2019

(54) COMPOUNDS FOR THE TREATMENT OF HPV-INDUCED CARCINOMA

(71) Applicant: Åbo Akademi, Åbo (FI)

(72) Inventors: Senthil Kumar Rajendran, Åbo (FI); Preethy Paul, Åbo (FI); Yury Brusentsev, Åbo (FI); Fang Cheng, Åbo (FI); Patrik Eklund, Åbo (FI); John Elias Eriksson, Åbo (FI)

(73) Assignee: Åbo Akademi, Åbo (FI)

( * ) Notice: Subject to any disclaimer, the term of this patent is extended or adjusted under 35 U.S.C. 154(b) by 0 days.

(21) Appl. No.: 15/504,696

(22) PCT Filed: Aug. 17, 2015

(86) PCT No.: PCT/FI2015/050532
§ 371 (c)(1),
(2) Date: Feb. 17, 2017

(87) PCT Pub. No.: WO2016/027005
PCT Pub. Date: Feb. 25, 2016

(65) Prior Publication Data
US 2017/0275263 A1    Sep. 28, 2017

(30) Foreign Application Priority Data
Aug. 17, 2014   (FI) .................................... 20145726

(51) Int. Cl.
| C07D 307/33 | (2006.01) |
| C07D 307/20 | (2006.01) |
| A61K 31/34 | (2006.01) |
| A61K 31/365 | (2006.01) |

(52) U.S. Cl.
CPC ............ *C07D 307/33* (2013.01); *A61K 31/34* (2013.01); *A61K 31/365* (2013.01); *C07D 307/20* (2013.01)

(58) Field of Classification Search
CPC ............................. C07D 307/20; C07D 307/33
See application file for complete search history.

(56) References Cited

FOREIGN PATENT DOCUMENTS

| WO | WO 2011109248 A1 | 9/2011 | |
| WO | WO 2013070566 A1 | 5/2013 | |
| WO | WO 2014/033366 | * 3/2014 | ............ A61K 31/365 |
| WO | WO 2014033386 A1 | 3/2014 | |

OTHER PUBLICATIONS

American Cancer Society (ACS), "Cancer facts & figures 2013", 2013.
Bray et al., "Globl cancer transitions according to the human development index (2008-2030): a population-based study", Lancet, Oncol, vol. 13, No. 8, Aug. 2012, pp. 790-801.
Finzer et al., "The role of human papillornavius oncoproteins E6 and E7 in apoptosis", Cancer Letters, 188, 2002, pp. 15-24.
Lipke, "An armamemtarium of wart treatments", Clinical Medicine & Research, vol. 4, No. 4. 2006. pp. 273-293.
Marshall et al., "Cembranolide total synthesis. Anisomelic acid", Tetrahedron, vol. 43, No. 21, 1987, pp. 4849-4860.
Marshall et al., "Stereoselective total synthesis of the cembranolide diterpene arisomelic acid", Tetrahedron Letters, vol. 27, No. 40, 1986, pp. 4873-4876.
Preethy et al., "Novel action modality of the diterpenoid anisomelic acid causes depletion of E6 and E7 viral oncoproteins in HPV-transformed cervical carcinoma cells", Biochemical Pharmacology. vol. 89, No. 2, Feb. 22, 2014, pp. 171-184.
Zeisser-Labouébe et al., "Screening of nanoparticle delivery systems for the photodection of cancer in a simple and cost-effective model", Nanomedicine 4, 2009, pp. 135-143.

* cited by examiner

*Primary Examiner* — Erich A Leeser
(74) *Attorney, Agent, or Firm* — Seppo Laine Oy

(57) ABSTRACT

A compound of Formula 1

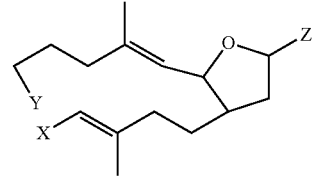

wherein,
X represents an alkyl, alkylene, alkenyl, alkenylene, alkynyl or alkynylene group,
optionally having at least one substituent selected from the group of —$OR^1$ and —$NR^1R^2$, or
Y represents —OTBS, —$OR^1$, —$NR^1R^2$;
Z represents —$OR^3$ or =O; and
$R^1$, $R^2$ and $R^3$ each independently stand for H, alkyl, alkenyl, alkynyl, aryl, heteroaryl, or heterocyclyl,
optionally in the form of enantiomers racemic mixtures, or pharmaceutically acceptable salts thereof, for use as a medicament, in particular for use in anti-viral cancer treatment in mammals and for use in treatment of benign or neoplastic genital Human Papilloma Virus associated diseases and for use in treatment of non-genital warts.

16 Claims, 4 Drawing Sheets

COMPOUNDS FOR THE TREATMENT OF HPV-INDUCED CARCINOMA

TECHNICAL FIELD

The present invention relates to compounds and to pharmaceutical uses thereof.

BACKGROUND ART

Cervical cancer is the second leading cause of cancer death in women and there are an estimated 529,000 new cases of cervical cancer and 275,000 deaths per year. In 2013, an estimated 12,340 new cases of invasive cervical cancer are expected to be diagnosed. In turn, the number of agents for the treatment of cervical cancer approved by the Food and Drug Administration (FDA) is very low, even with a dwindling trend over the past decade, (www.cancer.gov), demonstrating an urgent need for the development of new classes of compounds for treating cervical cancer. This need is accentuated by the predicted rise in cases of cervical cancer captured by improved screening and diagnostics, yielding an increase ranging from a few percent to 10% in all facets and stages of cervical cancer (www.bccresearch.com). This situation will not be alleviated by the ongoing anti-HPV vaccine trials, as the results of these will be seen only after several decades.

The main risk factor in cervical cancer is the oncogenic Human Papilloma Virus (HPV). The mechanisms through which HPV interferes with the normal life cycle of infected epithelial cells vary profoundly between high- and low-risk genotypes. In the case of high-risk genotypes, the late-expressed viral E6 oncoprotein is thought to bind specifically to the proteins coded by a couple of genes (p53 and the retinoblastoma tumor suppressor gene), which play a major role in the regulation of the cell cycle.

High-risk E6 also activates telomerase which prevents the erosion of telomeres and allows the host cell to continue through many rounds of division without damage to the DNA. E6 has also been reported to activate nuclear factor kappa B (NF-κB) leading to enhanced expression of Inhibitor of apoptosis protein 2 (IAP2) in HPV16 E6-immortalized human oral keratinocytes and primary human airway epithelial cells. It has also been observed that depletion of c-IAP2 leads to cell death, suggesting that HPV16-induced c-IAP2 expression is necessary for maintenance of the immortalized phenotype.

The E7 oncoprotein has also been implicated in HPV-mediated cancers. The E7 oncoprotein interacts with the cell cycle regulator pRb, inducing its proteolytic degradation, thereby preventing its binding to and inhibiting of the cell cycle promoting transcription factor E2F, with consequent stimulatory effect on cell cycle progression. In addition, E7 stimulates the expression of the S-phase cyclins, E and A, interacts with cyclin-kinase complexes, and abrogates the inhibitory activities of CKIs, such as p21Cip and p27Kip.

Therefore, blocking the activity of E6 and E7 oncoproteins serves as a prime therapeutic target in HPV-mediated cancers. Apart from cervical cancer, there is mounting evidence of HPV as a key causative agent in a number of other important cancers, including oral cancer, various head & neck cancers, as well as anogenital cancers. The established association of the E6 and E7 oncoproteins with many major types of cancer underscores the demand to find targeted treatments against these viral oncoproteins.

There are only 3 drugs (Bleomycin, Cisplatin and Hycamtin) that are approved by FDA against cervical cancer, all of which are known for poor specificity and serious side-effects (www.cancer.gov).

In terms of long-term cure of HPV-mediated cancers, vaccines provide a valid strategy. There are two vaccines (Gardasil and Cervarix) licensed and have been in the market (www.cancer.gov). These vaccines are efficient in preventing infection and, therefore, disease, but it will take decades before their real benefits are revealed and the vaccination coverage is restricted only to a number of well-developed countries. Patients not vaccinated who are already suffering from HPV-mediated cancers or who will still develop cancers, will have urgent needs for more efficient anti-cancer drugs. Due to recent misfortunes in the vaccine industry, the public acceptance for vaccination may also be rather variable. The vaccines will not have 100% penetrance, as they target do not cover all cancer-mediating HPVs.

Therefore, only a partial protection against cancer can be expected. Finally, these vaccines are expensive and will not be affordable for the public health management in all countries, especially not in developing countries. All of these aspects warrant an acute need for implementation of novel and affordable strategies to treat HPV-mediated cancers in the post vaccine era.

WO 2014/033366 discloses the use of anisomelic acid, a diterpenoid isolated from *Anisomeles malabarica* (L.) R. Br., for anti-viral cancer treatment. In WO 2014/033366, it is shown that anisomelic acid exhibits good efficiency in inducing apoptosis in HPV16 positive cervical cancer cells. Anisomelic acid inhibits protein level expression of E6 and E7, and thus is capable of acting as an anti-HPV agent.

Anisomelic acid is a hydrophobic compound which dissolves in DMSO and hot ethanol, and is mostly insoluble in water or other aqueous solvents. Low aqueous solubility of a drug may be a concern as it leads to poor bioavailability, high intrasubject/intersubject variability and lack of dose proportionality. To address that matter, WO2014/033366 discloses various approaches for achieving successful delivery of anisomelic acid containing drugs orally, such as solid dispersions, anti-solvents, complexation with cyclodextrin and lipid-based formulations, including lipid-based emulsion delivery systems, such as self-microemulsifying drug delivery systems (SMEDDS).

Another concern which relates to any natural substances is that synthesis of the molecules for the purpose of industrial-scale manufacture typically requires multistep processes with a number of separation and purification stages which influence the yield.

SUMMARY OF INVENTION

Technical Problem

It is an aim of the present invention to provide organic molecules, which can be used in anti-cancer therapy, in particular cervical cancer.

It is another aim of the invention to provide organic molecules which exhibit at least as good pharmaceutical effect as, and potentially higher therapeutic index than, anisomelic acid.

It is a third aim of the invention to provide organic molecules which exhibit at least as good pharmaceutical effect as, and potentially higher therapeutic index than, anisomelic acid and which in addition are more easily water-soluble.

It is a fourth aim of the invention to provide organic molecules which meet any of the preceding aims and which can be readily synthesized.

Solution to Problem

The present invention is based on the finding that compounds of Formula 1 exhibits good efficiency in inducing apoptosis in cervical cancer cells.

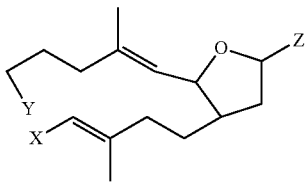

In formula 1,

X represents an alkyl, alkylene, alkenyl, alkenylene, alkynyl or alkynylene group, optionally having at least one substituent selected from the group of —OR$^1$ and —NR$^1$R$^2$;

Y represents —OTBS, —OR$^1$, —NR$^1$R$^2$;

Z represents —OR$^3$ or =O; and

R$^1$, R$^2$ and R$^3$ each independently stand for H, alkyl, alkenyl, alkynyl, aryl, heteroaryl, or heterocyclyl.

X and Y may also comprise optionally substituted imine groups.

Compounds of Formula 1 can be synthesized from suitable starting materials by synthesis routes described in the literature.

Compounds of Formula 1 are also suitable as intermediates, prodrugs and precursors of other pharmaceutically active compounds.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

Advantageous Effects of Invention

The present compounds exhibit good efficiency in inducing programmed cell death or apoptosis in cervical cancer cells and more specifically in HPV16-positive cervical cancer cells, as will be discussed in more detail below. The present compounds also exhibit good efficiency against oropharyngeal cancers. The mechanism of cell death has been found to be HPV-specific, as the same compound also inhibits protein level expression of E6 and cIAP2, both HPV-specific targets of HPV-positive cells. Therefore, the compound acts as an anti-HPV agent in HPV-positive cells.

Apart from the cellular studies, it is shown in the present invention that the cervical tumor growth on in vivo chick chorioallantoic membrane (CAM) can be effectively inhibited by at least a part of the present compounds.

For some embodiments it has been shown that anti-cancer and anti-viral activity is highly efficient at an early time point (2 hr)

Based on these findings, the present invention provides for novel compositions of compounds which can be used in anti-cancer therapy, in particular cervical cancer as well as head and neck cancers, such as oropharyngeal cancers.

The compounds can also be employed for methods to treat Human Papilloma Virus associated diseases, for example benign or neoplastic genital Human Papilloma Virus associated diseases, in particular Human Papilloma Virus mediated warts, genital warts as well as nongenital warts, comprising administering a therapeutically effective amount of compound of Formula 1 or their salts or derivatives thereof to said mammal.

Compounds of Formula 1, or their salts or derivatives thereof, can be topically administered to the mammal.

Furthermore, synthetic procedures are available which will help in synthesizing the present compounds with unprecedented efficiency. The present compounds are soluble in water. Nanocarriers are available for the targeted delivery

DESCRIPTION OF EMBODIMENTS

Figure 1:
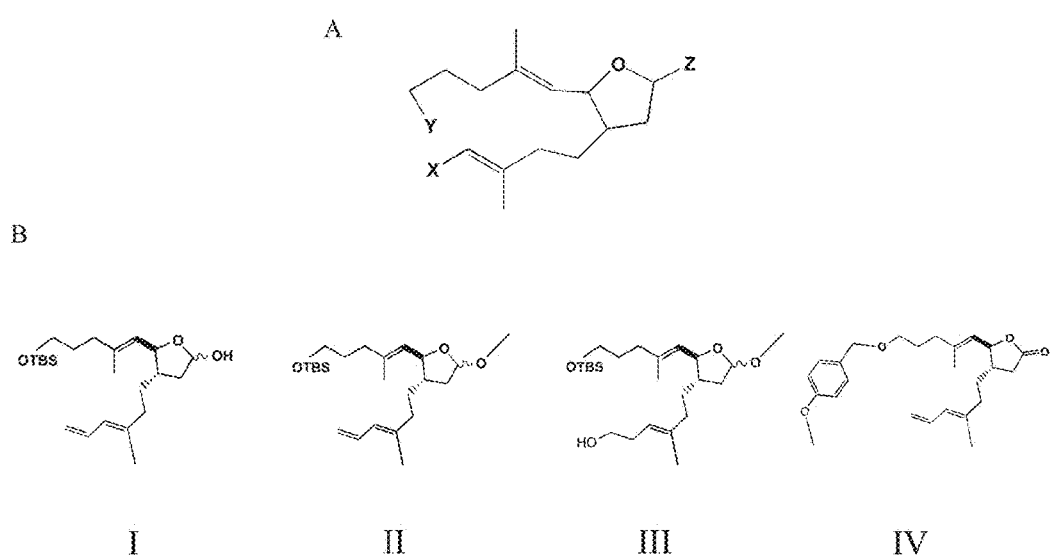
FIG. 1A shows the general formula of the present compounds (Formula 1)
FIG. 1B shows the structures of compounds I to IV.

As discussed above, compounds of Formula 1

Formula 1

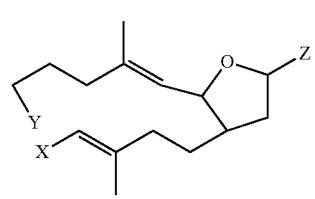

have been found to exhibit good efficiency in inducing apoptosis in cervical cancer cells and other cancer cells.

In Formula 1

X represents an alkyl, alkylene, alkenyl, alkenylene, alkynyl or alkynylene group, optionally having at least one substituent selected from the group of —OR$^1$ and —NR$^1$R$^2$;

Y represents —OTBS, —OR$^1$, —NR$^1$R$^2$;

Z represents —OR$^3$ or =O; and

R$^1$, R$^2$ and R$^3$ each independently stand for H, alkyl, alkenyl, alkynyl, aryl, heteroaryl, or heterocyclyl.

Isomers, such as enantiomers, as well as racemic forms, and pharmaceutically acceptable salt of the compounds and enantiomers and racemic forms are also included.

As used herein, the term "alkyl" refers to a saturated straight-chain (unbranched) or branched, cyclic, non-cyclic hydrocarbon having 1 to 10, preferably 1 to 5, carbon atoms.

The term alkyl may be further exemplified by groups such as methyl, ethyl, n-propyl, isopropyl, isobutyl, t-butyl, pentyl, pivalyl, heptyl, adamantyl, and cyclopentyl. Alkyl groups can either be unsubstituted or substituted with one or more substituents, for instance, halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

Throughout the description, the term "alkenyl" means a straight-chain or branched, non-cyclic hydrocarbon having 2 to 10, preferably 1 to 5, carbon atoms and having at least one carbon-carbon double bond. Typical examples of the straight-chain or branched (C2 to C10) alkenyl include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, and -3-decenyl. The alkenyl group may be substituted or not substituted.

Throughout the description, the term "alkynyl" means a straight-chain or branched, non-cyclic hydrocarbon having 2 to 10, preferably 2 to 5, carbon atoms and having at least one carboncarbon triple bond. Typical examples of the straight-chain or branched (C2 to C10) alkynyl include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, and -9-decynyl. The alkynyl group may be substituted or not substituted.

"Alkylene", "alkenylene" and "alkynylene" stands for bifunctional radicals corresponding to the above "alkyl", "alkenyl" and "alkynyl" groups, respectively.

Particularly preferred groups are ethylene substituted with —OR$^1$ or —NR$^1$R$^2$ (—CH$_2$CH$_2$—X$^1$, wherein X$^1$ stands for —OR$^1$ or —NR$^1$R$^2$, wherein R$^1$ and R$^2$ have the same meanings as above) and alkenyl groups, such as vinyl (—CH═CH$_2$).

Throughout the description, the term "aryl" means a carbocyclic aromatic group having 5 to 10 ring atoms. Typical examples thereof include, but not limited to, phenyl, tolyl, anthracenyl, fluorenyl, indenyl, azulenyl, pyridinyl, and naphthyl, and also include benzo-fused carbocyclic moieties such as 5,6,7,8-tetrahydronaphthyl. The carbocyclic aromatic group may be substituted or not substituted. In one embodiment, the carbocyclic aromatic group is a phenyl group.

Throughout the description, the term "heteroaryl" means a 5 to 10-membered aromatic heterocycle having at least one hetero atom selected from nitrogen, oxygen, and sulfur atoms and having at least one carbon atom and includes both monocycle and bicycle. Typical examples of the heteroaryl include triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzoimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thiethanyl, and oxazolyl.

Throughout the description, the term "heterocyclyl" means saturated or unsaturated 5 to 7-membered monocyclic or 7 to 10-membered bicyclic heterocycle having 1 to 4 hetero atoms independently selected from nitrogen, oxygen, and sulfur atoms, wherein the nitrogen and sulfur hetero atoms are optionally oxidized, and the nitrogen hetero atom is optionally quaternized, and includes a bicycle formed by condensation of any of these heterocyclyls to a benzene ring. The heterocyclyl can bond via an appropriate hetero atom or carbon atom.

The heteroaryls defined above are included in the heterocyclyl. Typical examples of the heterocyclyl include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, and tetrahydrothiopyranyl.

In one embodiment, in Formula 1, OTBS stands for a silyl group, in particular tert-butyldimethylsiloxy group.

In another embodiment, which can be combined with the previous, OTBS stands for a protecting group.

Particularly preferred embodiments, comprise compounds of Formula 1, wherein X stands for an ethylene group substituted with a hydroxyl group, or for a vinyl group, Y represents —OTBS and Z stands for —OR$^3$ or ═O, wherein R$^3$ is a linear or branched alkyl group having 1 to 4 carbon atoms.

Particularly interesting compounds are represented by compounds according to Formula 1a

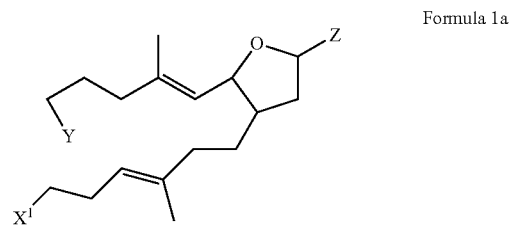

Formula 1a wherein
X$^1$ represents —OR$^1$, —NR$^1$R$^2$;
Y represents —OTBS, —OR$^2$, —NR$^1$R$^2$;
Z represents —OR$^3$ or ═O; and
R$^1$, R$^2$ and R$^3$ each independently stand for H, alkyl, alkenyl, alkynyl, aryl, heteroaryl, or heterocyclyl.

Based on the above, three particularly interesting embodiments comprise molecules of formulas I to IV:

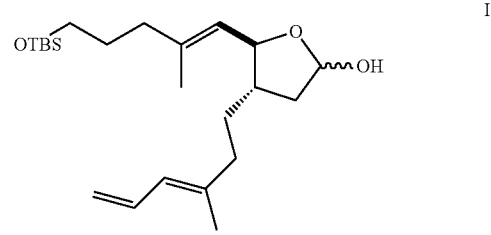

I

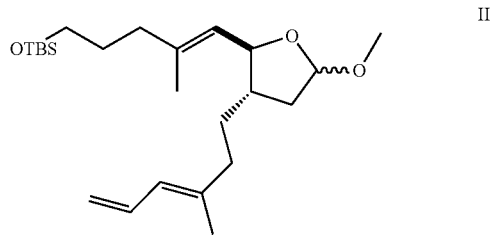

II

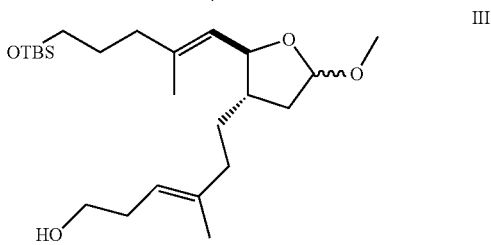

III

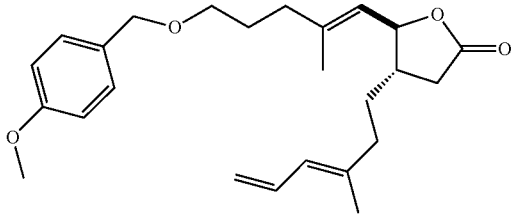

Compound I: 5-[(E)-5-[tert-butyl(dimethyl)silyl]oxy-2-methyl-pent-1-enyl]-4-[(3E)-3-methylhexa-3,5-dienyl]tetrahydrofuran-2-ol;

Compound II: tert-butyl-[(E)-5-[5-methoxy-3-[(3E)-3-methylhexa-3,5-dienyl]tetrahydrofuran-2-yl]-4-methyl-pent-4-enoxy]-dimethyl-silane; and Compound III: (E)-6-[2-[(E)-5-[tert-butyl(dimethyl)silyl]oxy-2-methyl-pent-1-enyl]-5-methoxy-tetrahydrofuran-3-yl]-4-methyl-hex-3-en-1-ol.

Compound IV: (4S,5S)-5-[(E)-5-[(4-methoxyphenyl)methoxy]-2-methyl-pent-1-enyl]-4-[(3E)-3-methylhexa-3,5-dienyl]tetrahydrofuran-2-one and the enantiomer.

In compounds I to III, OTBS represents tert-butyldimethylsiloxy, a silyl group typically used as a protecting group. It can be removed to yield a hydroxyl group at the corresponding site. Thus, compounds I to IV, as well as generally compounds of Formula 1, are suitable also as precursors and prodrugs for therapeutically active compounds.

The wiggly lines in Formulas I to IV indicate that the molecules are racemic mixtures.

Within the scope of the present invention, enantiomerically pure isomers of any compounds of Formula 1 are, however, also included, in particular the R- and S-isomers of general Formula 1, such as the R- and S-isomers of Formulas I to IV.

Throughout the description, the term "pharmaceutically acceptable salt" means a salt prepared from a pharmaceutically acceptable non-toxic acid or base, of which examples include inorganic acids and bases and organic acids and bases. Examples of the pharmaceutically acceptable base addition salt suitable for the compound of the present invention include, but not limited to, metal salts formed from aluminum, calcium, lithium, magnesium, potassium, sodium, and zinc; and organic salts formed from lysine, N,N'-dibenzylethylenediamine, chloroprocaine, choline, diethanolamine, ethylenediamine, meglumine (N-methylglucamine), and procaine.

Examples of the suitable non-toxic acid include, but not limited to, inorganic and organic acids, such as acetic acid, alginic acid, anthranilic acid, benzenesulfonic acid, benzoic acid, camphorsulfonic acid, citric acid, ethenesulfonic acid, formic acid, fumaric acid, furoic acid, galacturonic acid, gluconic acid, glucuronic acid, glutamic acid, glycolic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phenylacetic acid, phosphoric acid, propionic acid, salicylic acid, stearic acid, succinic acid, sulfanilic acid, sulfuric acid, tartaric acid, and ptoluenesulfonic acid. Specific examples of the non-toxic acid include hydrochloric acid, hydrobromic acid, phosphoric acid, sulfuric acid, and methanesulfonic acid. Accordingly, specific examples of the salt include hydrochlorides and mesylates. Other salts are known in the art and are described in, for example, Remington's Pharmaceutical Sciences, 18th Eds.

The compound or a pharmaceutically acceptable salt thereof of the present invention may be in a solvate, hydrate, clathrate, or prodrug form.

Herein, the term "solvate" means the compound or a salt thereof of the present invention further including a stoichiometric or non-stoichiometric amount of solvent bound by non-covalent intermolecular forces. The solvent is preferably volatile, non-toxic, and/or compatible with administration to human in a very small amount.

The term "hydrate" means the compound or a salt thereof of the present invention further including a stoichiometric or non-stoichiometric amount of water bound by non-covalent intermolecular forces.

The term "enantiomer" refers to one of two stereoisomers that have mirror images of one another.

The term "racemate" refers to means a mixture of equal amounts of enantiomers of a chiral molecule.

The term "diastereomer" refers to one of a class of stereoisomers that are not enantiomers, but that have different configurations at one or more of the equivalent chiral centers. Example of diasteromers are epimers that differ in configuration of only one chiral center.

The term "stereoisomer" refers to one of a class of isomeric molecules that have the same molecular formula and sequence of bonded atoms, but different three-dimensional orientations of their atoms in space.

The term "tautomer" refers to isomeric molecules that readily interconvert by a chemical reaction. The reaction commonly results in the migration of a hydrogen atom, which results in a switch of a single bond and adjacent double bond.

The term "associated" when used in connection with the expression "Human Papilloma Virus associated diseases" implies that there is a causal association between HPV and the diseases. Thus, "associated" covers various HPV-induced and HPV-mediated diseases. Such diseases are caused for example by an HPV infection.

A prodrug is a medication that is administered as an inactive (or less than fully active) chemical derivative that is subsequently converted to an active pharmacological agent in the body, often through normal metabolic processes.

As will become evident from the results section, the present compounds, exemplified by compounds I to IV exhibits good efficiency in inducing apoptosis in HPV16-positive cancer cells, including cervical cancer cells and oropharyngeal cancer cells.

The present compounds are also efficient in down-regulating viral oncoproteins E6 and E7 that are the oncoproteins responsible for HPV-mediated cervical carcinogenesis thus acting as an anti-HPV and anti-cancer agent. Similarly, the present compounds are efficient in treatment of other HPV-mediated cancers, including oropharyngeal cancers.

Further, the present compounds, in particular compound III, induce apoptosis by down-regulating cIAP2 at an early time point (2 hr).

Compound III also induces apoptosis by activation of caspase 3 and PARP cleavage at an early time point (2 hr). Compound III effectively inhibits tumor growth on CAM model.

Further, the present compounds can be used in methods of treating or preventing cancer or a similar condition in a mammal wherein the p53 pathway is deregulated by viral oncoproteins by administration of a therapeutically effective amount of compound of Formula 1 or their salts or derivatives thereof to said mammal.

The compounds can also be used for down-regulating oncoproteins and cellular inhibitor of apoptosis protein 2 (c-IAP2).

Cell cycle arrest can be reactivated by activating p53-p21 pathway and also inducing p53-independent apoptosis.

The present compounds can be prepared and characterized based on the stereoselective method previously described by Marshall & DeHoff.

Scheme 1 (below) illustrates a broad presentation of a mechanism of synthesizing various compounds of the disclosure.

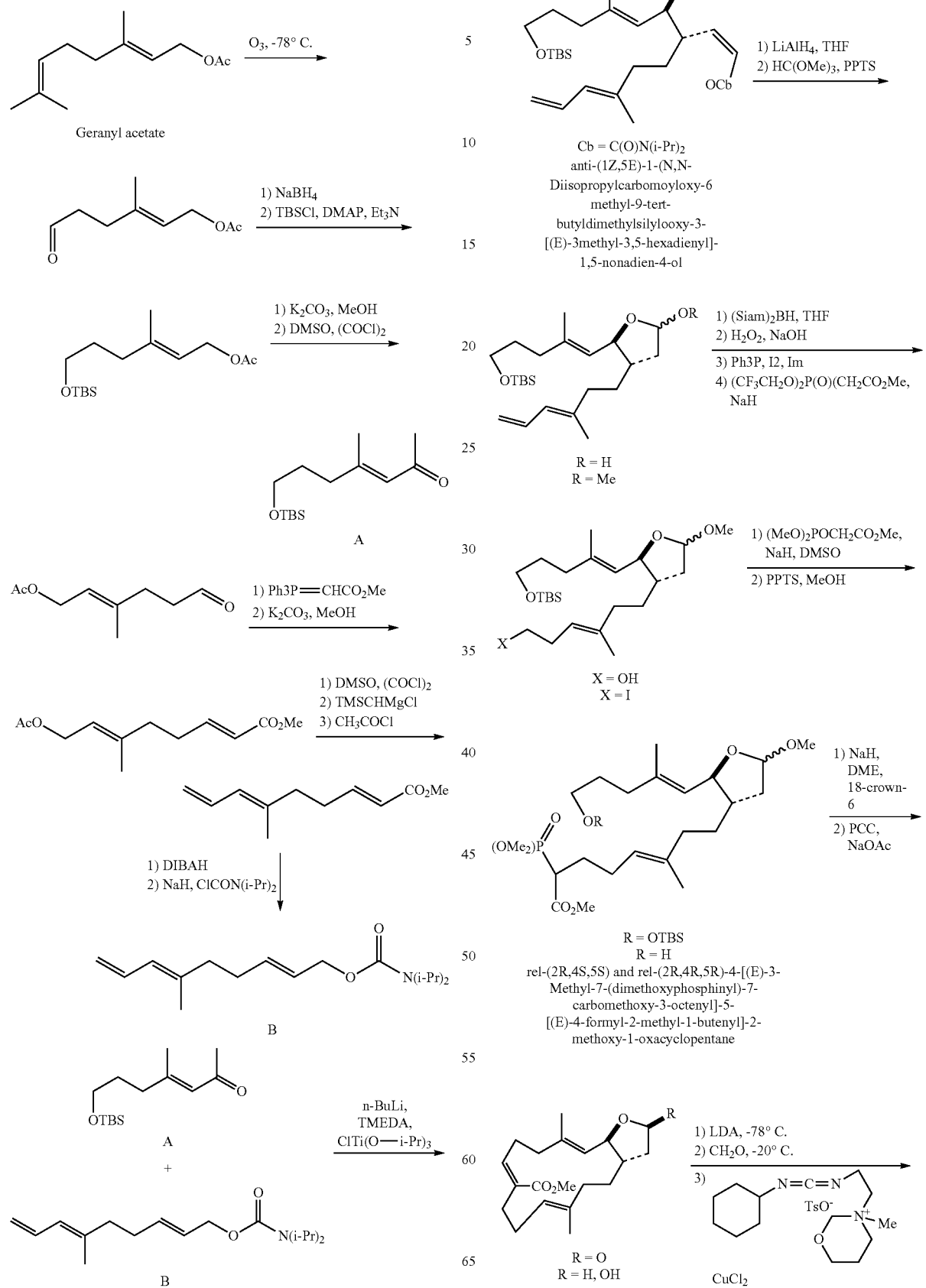

11
-continued

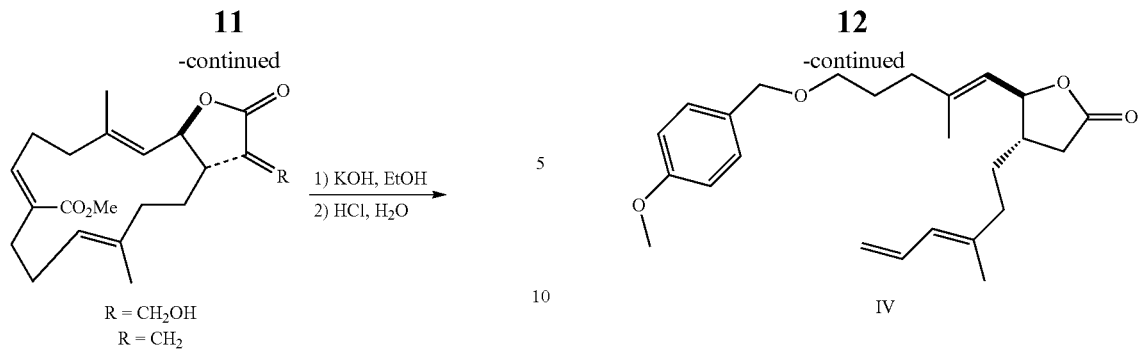

R = CH₂OH
R = CH₂

Scheme 2 (below) illustrates a broad presentation of a mechanism of synthesizing compound IV of the disclosure.

Scheme 2

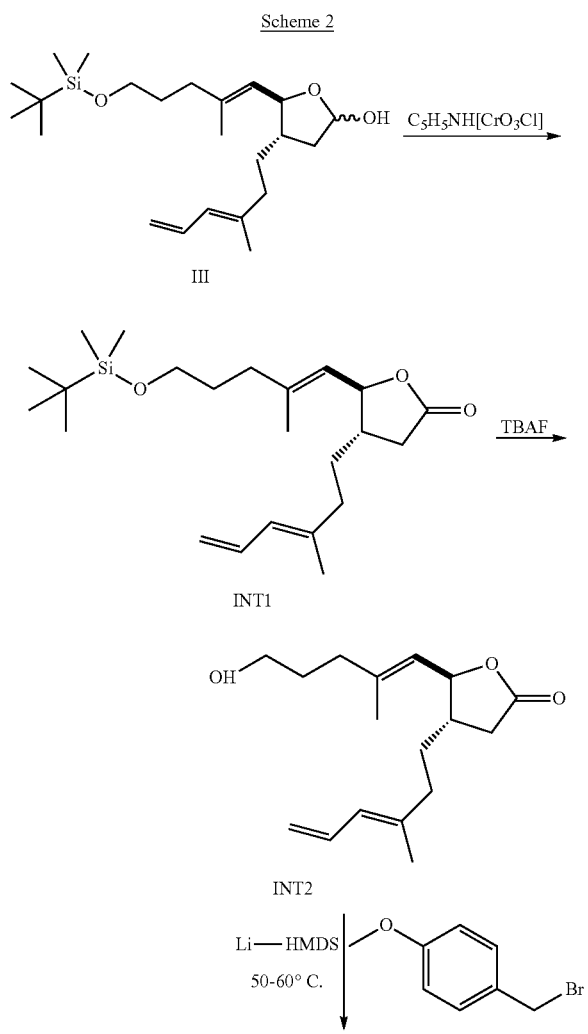

12
-continued

IV

The active components are used in effective amounts.

The route of administration, the dosage as well as the exact formulation are chosen depending on the subject's condition. Thus, the interval can be adjusted individually to provide levels of the active compound in the blood plasma that are sufficient to maintain and obtain the desired therapeutic effects. In general, however, doses employed for humans typically are in the range of 0.001 mg/kg to about 1000 mg/kg per day, preferably in the range of about 0.1 mg/kg to about 500 mg/kg per dose of inhibitor.

Typically, the present compounds are administered at 0.001 to 100 mg/kg body weight, for example at 0.01 to 50 mg/kg body weight. In some embodiments, they can be employed in doses ranging from about 0.1 to about 50 mg/kg, about 0.5 to about 40 mg/kg or about 0.7 to about 30 mg/kg. Specific doses contemplated include sub-ranges of any of the foregoing ranges in 0.1 mg/kg increments.

The pharmaceutical composition will comprise the present compounds either as the primary or as the sole therapeutically efficient component (or agent). Therefore, within the scope of the present technology, compositions are also provided wherein the effective agent consists of or consists essentially of compounds of Formula 1 and salts thereof. Naturally, it is possible to combine compounds of Formula 1 with other anticarcinogenic compounds, such as tyrosine kinase inhibitors, such as Pazopanib, and angiogenetic agents, such as vascular endothelial growth factor inhibitors, e.g. Bevacizumab, and with anisomelic acid and derivatives thereof.

The pharmaceutical compositions can be in any suitable form. Typical pharmaceutical forms include aqueous, oleaginous suspension, dispersions as well as sterile powders, which may be used for the extemporaneous preparation of injectable solutions or dispersions. It can be used for topical (e.g. intravaginal) application, for example in the form of intravaginal creams or by application of prolonged release solid preparations, such as sustained release pharmaceutical plasters. The compositions may also be solutions or suspensions in non-toxic diluents or solvents, e.g. as solutions in 1,3-butanediol.

Alternatively, they can be prepared as microemulsions and administered, for example orally.

The carrier can be a solvent or dispersion medium containing, for example, water, polyol (for example, glycerol, propylene glycol, and liquid polyethylene glycol, and the like), ethanol, and mixtures of the indicated components, various vegetable oils, Ringer's solution and isotonic sodium chloride solutions. In addition, fixed oils may be employed as a solvent or suspending medium. Fixed oils that can be employed include synthetic mono- or diglycerides. Further, fatty acids such as oleic acid find use in the preparation of injectables.

As conventional, the pharmaceutical composition may contain formulation materials for modifying, maintaining or preserving, for example, the pH, osmolality, viscosity, clarity, color, isotonicity, odor, sterility, stability, rate of dissolution or release, adsorption or penetration of the composition.

The pharmaceutical compositions can also be selected for inhalation or for delivery through the digestive tract, such as orally. The preparation of such pharmaceutically acceptable compositions is within the skill of the art. The present compounds can be present in the same pharmaceutical composition. They can also be comprised in different pharmaceutical compositions which are, for example, supplied in the same package.

Although the above description primarily relates to human objects, pharmaceutical compositions for veterinary use are also included herein.

The following non-limiting examples illustrate embodiments of the present technology.

EXAMPLES

Example 1

Preparation of Compounds

Unless otherwise stated, chemicals were obtained from commercial suppliers and used without further purification. THF was dried by the sodium-benzophenone method immediately prior to use. NMR spectra were recorded with Bruker Avance 600 MHz spectrometer using standard pulse sequences. LCMS data was obtained using Agilent 1100 equipped with Ion Trap mass detector with ESI (electrospray ionization) operated in positive mode. The reactions were monitored by TLC. Aluminum based TLC plates (Merck) silicagel 60 $F_{254}$ were used.

Compounds I to III were prepared based on the stereoselective method previously described by Marshall & DeHoff by using as starting materials a compound of building block A or B in Scheme 1. Both A and B are prepared from geranyl acetated by processes known in literature.

Compound IV (Scheme 2) was prepared as follows.

Intermediate INT1:

Compound III (680 mg, 1.723 mmol) was dissolved in dichloromethane (20 ml) and Pyridinium chlorochromate (431 mg, 2 mmol) was added in one portion. The mixture was stirred for 3 h at room temperature. Then the mixture was diluted with 30 ml of diethyl ether and filtered through a pad of celite and the filtrate was evaporated to dryness. The residue was purified by flash chromatography in chloroform to give compound INT1 (570 mg, 84.2% yield) as a colorless oil.

Intermediate INT2:

Compound INT1 (570 mg, 1.45 mmol) was dissolved in Tetrahydrofuran (50 ml) and Tetrabutylammonium fluoride 1M solution in Tetrahydrofuran (2.9 ml, 2.9 mmol) was added in one portion. The reaction mixture was stirred overnight at room temperature. Then the reaction mixture was diluted with 50 ml of saturated ammonium chloride water solution and extracted with Ethyl acetate (3×50 ml). The combined organic extracts were dried with sodium sulfate and concentrated in vacuo. The residue was purified by column chromatography on silica (eluent Chloroform/Acetone 10:1) to give the compound INT2 (309 mg, 76% yield) as colorless oil.

Compound IV: Intermediate INT2 (200 mg, 0.68 mmol) was dissolved in Dimethylformamide (3 ml) and cooled down to −20° C. Then 1M solution of Lithium Bis(trimethylsilyl)amide in Tetrahydrofuran (0.68 m, 0.68 mmol) was added dropwise. The reaction mixture was stirred at −20° C. for 20 min and then 4-methoxy-benzylbromide (128 mg, 0.75 mmol) was added. Cooling was removed and the reaction mixture was stirred overnight at room temperature and then diluted with water (15 ml) and extracted with Diethyl ether (3×15 ml). The organic extracts were combined, washed with water (3×30 ml) and brine (30 ml), dried with sodium sulfate and then concentrated to dryness. The residue was purified by column chromatography on silica (eluent Ethyl acetate/Hexanes 1:10) to give the compound IV (110 mg, 41.3% yield) as colorless oil. $^1$H NMR (600 MHz, $CDCl_3$) δ ppm 1.41-1.52 (m, 1 H) 1.61-1.71 (m, 1 H) 1.71-1.74 (m, 2 H) 1.75 (s, 3 H) 1.76 (d, J=1.13 Hz, 3 H) 1.98-2.12 (m, 2 H) 2.16 (t, J=7.37 Hz, 2 H) 2.19-2.27 (m, 1 H) 2.34-2.39 (m, 1 H) 2.70 (dd, J=17.00, 7.93 Hz, 1 H) 3.45 (t, J=6.42 Hz, 2 H) 3.82 (s, 3 H) 4.41-4.46 (m, 2 H) 4.79 (t, J=8.69 Hz, 1 H) 4.97-5.07 (m, 1 H) 5.13 (d, J=16.62 Hz, 1 H) 5.19 (d, J=8.69 Hz, 1 H) 5.84 (d, J=10.58 Hz, 1 H) 6.56 (dt, J=16.71, 10.53 Hz, 1 H) 6.90 (dt, J=8.69, 2.27 Hz, 2 H) 7.27 (dt, J=8.70, 2.27 Hz, 2 H) $^{13}$C NMR (151 MHz, $CDCl_3$) δ ppm 166.4, 17.0, 27.7, 30.0, 30.2, 30.3, 35.5, 36.0, 55.3, 69.2, 72.6, 82.2, 113.8, 113.8, 115.6, 122.0, 126.3, 129.3, 129.3, 130.6, 132.9, 137.7, 143.9, 159.2, 176.4

LCMS

A sample of compound IV was analyzed by LC-MS (column Agilent ZORBAX Eclipse XDB-C8; mobile phase: Acetonitrile (A), 0.5% TFA in $H_2O$ (B); flow rate: 0.7 ml/min) using linear gradient (50%-95%). (+)-ESI-MS (m/z 200-1600) of the most intense ion of the MS range ($t_R$ 10.8 min) m/z 399 [M+H] was obtained.

Example 2

Cell Culture and Treatments

SiHa cervical cancer cells were and cultured in DMEM (Sigma-Aldrich, St Louis, Mo., USA). The medium was supplemented with 10% fetal calf serum (BioClear, Wiltshire, UK), 2 mM Lglutamin, 100 U/ml penciliin, 100 μg/ml streptomycin (Sigma-Aldrich).

Example 3

Detection of Apoptotic Parameters

SiHa cells were treated with 0-40 μM compounds. 24 hours later, the cells were collected and analyzed for apoptosis and/or necrosis. Activated caspase-3 in cells was labeled with phycoerythrin-conjugated antibody according to manufacturer's protocol (PE Active Caspase-3 Apoptosis Kit; BD Pharmingen, San Diego, Calif.) and analyzed by FACSCalibur flow cytometer (FL-2, FSC, BD Pharmingen).

Flow cytometric analysis of apoptosis was performed on cells that were plated on a 96-well plate as triplicate samples. The cells were pretreated with different concentrations of compound III for 0-6 hour after which the plate was centrifuged with a culture plate rotor (1000 rpm, 5 minutes). For analysis of nuclear fragmentation, propidium iodide (PI) buffer (40 mM Na-citrate, 0.3% Triton X-100, 50 μg/ml PI; Sigma) was added to the wells. After 10 minutes incubation at room temperature, the plate was analyzed with LSRII flow cytometer equipped with HTS platform (PE-A channel). The fraction of sub-G0/G1 events (nuclear fragmentation) was gated as a measure of apoptotic cell death.

Example 4

Western Blotting

Whole cell lysates were prepared by lysing floating and attached cells in Laemmli sample buffer and boiling the samples for 10 minutes. Proteins were separated by SDS-PAGE and transferred on PVDF membrane (Millipore). Western blotting was performed using antibodies against Caspase 3 (Cell Signalling Technology), poly (ADP-ribose) polymerase (clone C-2-10; Sigma-Aldrich), HPV16 E6 (N-17) (Santa Cruz), cIAP2 (Santa Cruz) and Actin (clone AC-40; Sigma-Aldrich). HRP-conjugated secondary antibodies were from Southern Biotechnology Associates, Promega, and Amersham Biosciences. The results were visualized using the ECL method (Amersham Biosciences) on X-ray film.

Example 5

In Ovo Chick Chorioallantoic Membrane (CAM) Model

The CAM was prepared according to previously described method. Fertilized white leghorn chicken eggs were obtained from LSK Poultry Oy, Finland. The eggs were disinfected with 70% ethanol and transferred into a hatching incubator (Savimat MG 200, Chauffry, FR) at 37° C. 65% relative humidity with automatic turning for 3 days. On embryonic development day (EDD) 3, a hole of approximately 3 mm in diameter was drilled into the egg-shell and covered with Parafilm® (Pechiney, Menasha, USA) and then returned to the incubator until use. On EDD 8, the hole in the shell was extended to approximately 3 cm in order to provide better access for tumor cell implantation. A polyethylene ring (approximately 0.5 mm think and 7 mm inner diameter) was deposited on the CAM. Then, $1.5 \times 10^5$ SiHa cells were seeded inside the ring on the CAM together with growth factor reduced Matrigel (BD Biosciences, USA) that had been mixed in a 1:1 ratio with serum free DMEM media. After implantation, the egg-shell was covered again and returned to the incubator. For the CAM assay, the different doses (0-6 mg/kg) of compound III were added topically (20 µL) to the CAM tumors from EDD 9-13, with additions taking place at the same time on all the days. The tumor xenografts were harvested from the CAM membrane and weighed on EDD 14. The results were repeated at least 3 times. In each experiment, the results of 7-10 eggs per compound dose were evaluated.

Example 6

Morphologic Staining and Immunohistochemistry

Five-micrometer-thick sections were taken perpendicularly from paraffin-fixed CAM tumors samples and processed for H&E staining. Images were taken with a DC300F digital camera attached to a DMLB microscope (Leica). For immunohistochemistry analysis of tissue sections, upon antigen revealing, tissues were immunohistochemically stained with HRP conjugated antibody and visualized by using ABC staining system (Vector lab, CA, USA). Finally all sections were counterstained with Mayers hematoxyline (Histolab, Gothenburg, Sweden).

Isotype and concentration matched primary antibodies were used as negative controls, and all were found to be negative.

Results

The embodiment of the present invention relates to novel use of compound of Formula I, or a pharmaceutically acceptable salt or a derivative thereof as an active ingredient; and use thereof for anti-cervical cancer and anti-oropharyngeal cancer treatment and anti-viral treatment in mammals.

Figure 2:
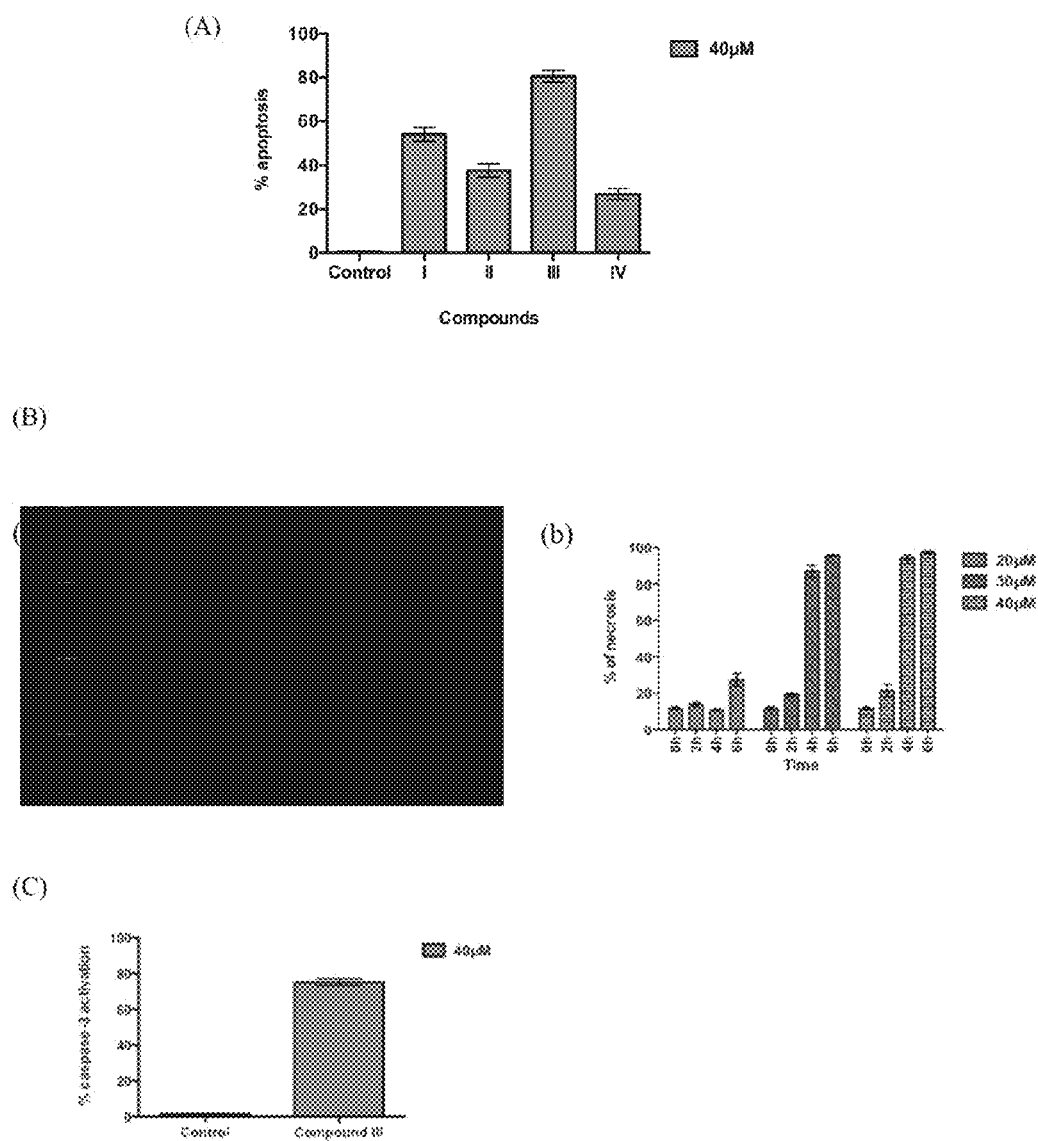
FIG. 2. (A). SiHa cells were incubated with 40 μM of compounds I to IV for 24 h. After incubation, the percentage of apoptotic cells with propidium Iodine (PI) were detected by flow cytometry (B) Percentage of apoptosis (a) and necrosis (b) induced by compound III in a dose and time dependent manner in SiHa cells. (C) Caspase 3 activation by compound III in SiHa cells at 2 h.

In order to discover the capacity of compounds to sensitize HPV mediated SiHa cervical cancer cells to apoptosis, we assayed four compounds I, II, III and IV (FIG. 1B). The cells were treated with compounds initially for 24 h after which the cells were analyzed for caspase 3 activation. The results reported herein show that all the three compounds are cytotoxic to SiHa (FIG. 2A).

However, compound III was found to be highly effective and hence was subjected to nuclear fragmentation assay using a LSRII flow cytometer HTS-unit in 96-well format for analyzing the effect in a time and dose dependent manner. The formation of propidium iodide labeled DNA fragments (FIG. 2) was used as the primary indicator of apoptotic cell death. To further confirm the apoptotic effect of compound III in SiHa cells, we performed Western blot to assess the proteolytic cleavage of procaspase-3, PARP and expression of the HPV oncoprotein, HPV16 E6.

Figure 3:
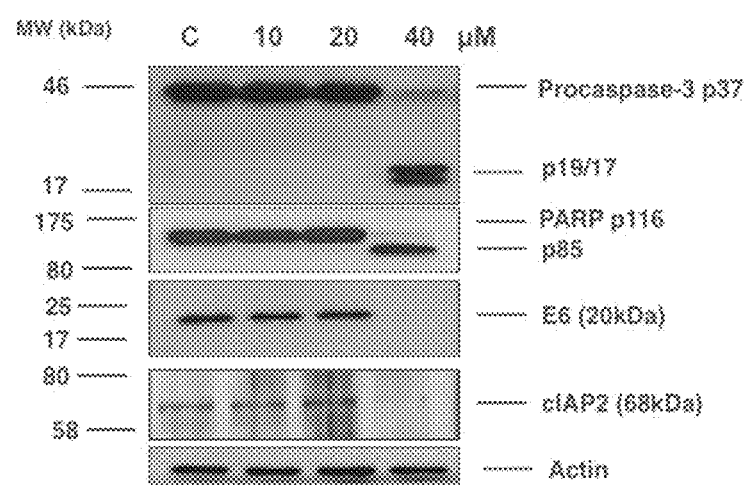
FIG. 3. Western blot analysis of various proteins after treatment with 40 μM compound III at 2 h.

The result demonstrates that 40 µM compound III cleaves caspase-3, PARP and downregulates E6 and cIAP2 at 2 h itself (FIG. 3), revealing the effect of compound III at an earlier time point. These results clearly show that compound III is highly effective in inducing apoptosis.

Figure 4:
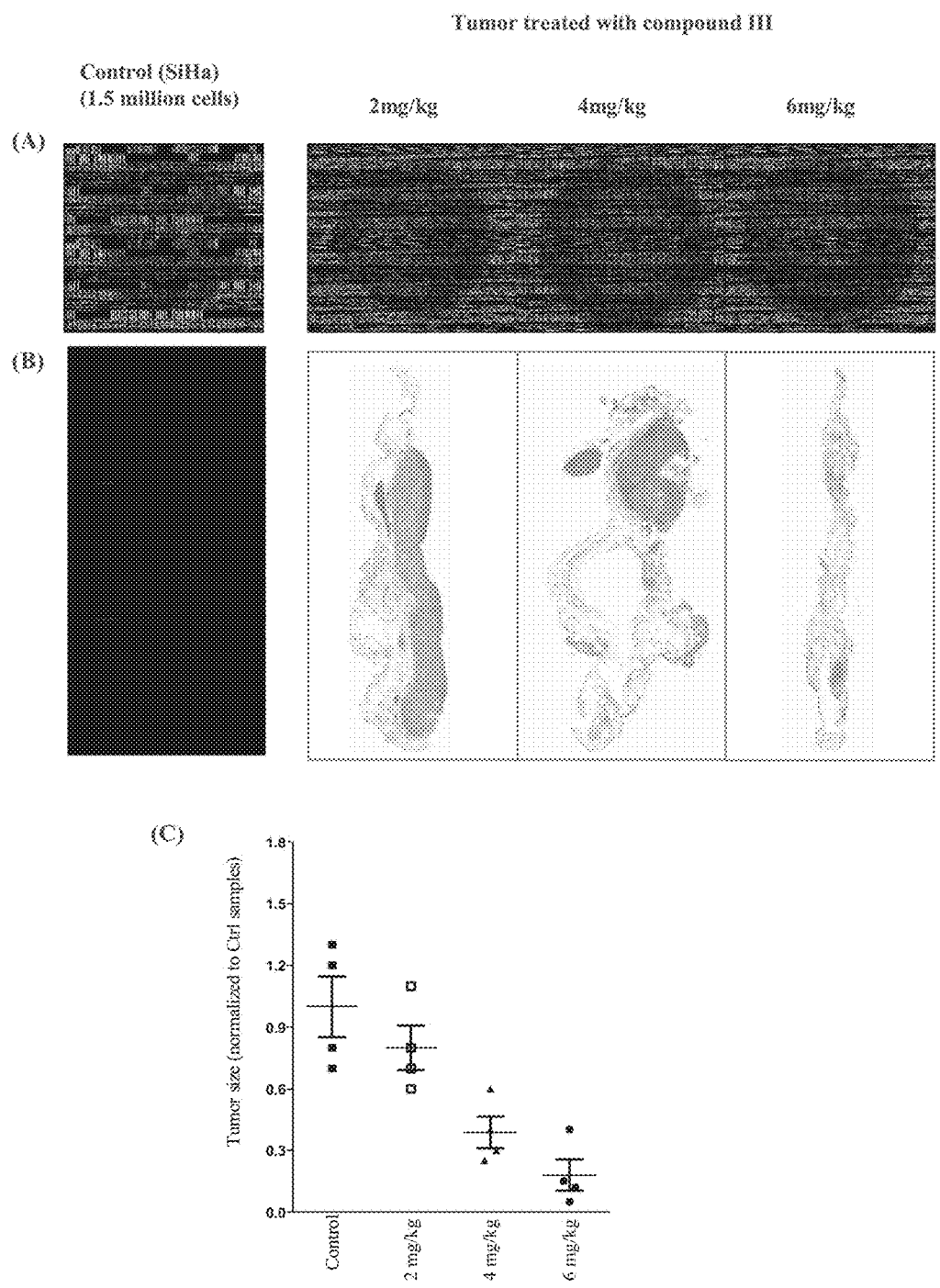
FIG. 4. (A) Compound III inhibits the growth of SiHa cells in the CAM in vivo tumor growth model. (B) Representative pictures of H&E staining of SiHa tumor cells in the CAM in ovo tumor growth model upon different concentration of compound III treatment (±s.e.m.; n=4). (C) Quantification of SiHa tumor size indicated in panel.

The CAM model can be employed to study the preliminary in vivo efficacy of compound III. The efficacy of compound III was tested by topical administration on cervical tumors (SiHa) grown on CAM. The dose-dependent inhibition of SiHa, cervical tumor growth on CAM by compound III is shown in FIG. 4. While the SiHa cells in the CAM model rapidly formed a prominent tumor, already a dose of 4 mg/kg inhibited the tumor growth and 6 mg/kg was able to deplete an already formed tumor (FIG. 4A). The efficacy of compound III on tumor growth inhibit was further confirmed by hematoxylin/eosin (H&E) stainings as well as immunohistochemistry using proliferation and apoptotic markers (FIG. 4B-C and data not shown). As shown in the FIG. 4B, the representative control section showed densely populated tumor cells all over the CAM tissue, while at doses 2 mg/ml of compound III, the regression of tumor growth was beginning to be evident.

The compound III effect is in a dose-dependent manner as at 4 mg/ml tumor size was significantly smaller than control sample and at 6 mg/ml the tumor was almost completed regressed. The quantitation results from FIG. 4C further confirmed that compound III induce cell apoptosis in a dose-dependent manner using an in ovo tumor model.

The following embodiments are characteristic of the present invention:

1. A compound of Formula 1

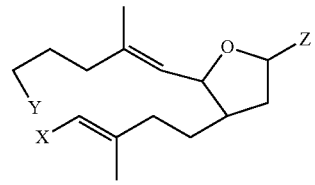

wherein,

X represents an alkyl, alkylene, alkenyl, alkenylene, alkynyl or alkynylene group, optionally having at least one substituent selected from the group of —OR¹ and —NR¹R²;

Y represents —OTBS, —OR¹, —NR¹R²;

Z represents —OR³ or =O; and

R¹, R² and R³ each independently stand for H, alkyl, alkenyl, alkynyl, aryl, heteroaryl, or heterocyclyl, or a pharmaceutically acceptable salt thereof, for use as a medicament.

2. A compound of Formula 1

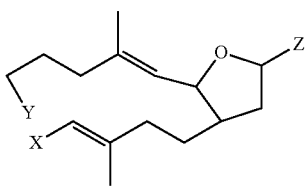

wherein,

X represents an alkyl, alkylene, alkenyl, alkenylene, alkynyl or alkynylene group, optionally having at least one substituent selected from the group of —OR¹ and —NR¹R²;

Y represents —OTBS, —NR¹R²;

Z represents —OR³ or =O; and

R¹, R² and R³ each independently stand for H, alkyl, alkenyl, alkynyl, aryl, heteroaryl, or heterocyclyl, or a pharmaceutically acceptable salt thereof, for use in anti-viral cancer treatment in mammals, for use in treatment of Human Papilloma Virus associated diseases, such as of benign or neoplastic genital Human Papilloma Virus associated diseases, or for use in treatment of non-genital warts.

3. The compound of embodiment 2 for use in treatment of Human Papilloma Virus mediated genital warts.

4. The compound of embodiment 2 or 3, wherein X stands for a hydroxyl group, Y represents —OTBS and Z stands for —OR³ or =O, wherein R³ is a linear or branched alkyl group having 1 to 4 carbon atoms.

5. The compound of any of embodiments 2 to 4, which is selected from the group of 5-[(E)-5-[tert-butyl(dimethyl)silyl]oxy-2-methyl-pent-1-enyl]-4-[(3E)-3-methylhexa-3,5-dienyl]tetrahydrofuran-2-ol;

tert-butyl-[(E)-5-[5-methoxy-3-[(3E)-3-methylhexa-3,5-dienyl]tetrahydrofuran-2-yl]-4-methyl-pent-4-enoxy]-dimethyl-silane;

(E)-6-[2-[(E)-5-[tert-butyl(dimethyl)silyl]oxy-2-methyl-pent-1-enyl]-5-methoxy-tetrahydrofuran-3-yl]-4-methyl-hex-3-en-1-ol; and (4S,5S)-5-[(E)-5-[(4-methoxyphenyl)methoxy]-2-methyl-pent-1-enyl]-4-[(3E)-3-methylhexa-3,5-dienyl]tetrahydrofuran-2-one and the enantiomer 6. The compound according to any of embodiments 1 to 5 in the form of a racemic mixture or as enantiomers, in particular R- or S-enantiomers thereof.

7. A pharmaceutical composition for use in anti-viral cancer treatment in mammals, comprising a therapeutically effective amount of compound of Formula 1, optionally in the form of a racemic mixture or as enantiomers, or salts or derivatives thereof, in particular the therapeutically effective compound of the composition consists essentially of a therapeutically effective amount of compound of Formula 1, optionally in the form of a racemic mixture or as enantiomers, or salts or derivatives thereof.

8. A pharmaceutical composition for use in treatment of benign or neoplastic genital Human Papilloma Virus associated diseases, in particular Human Papilloma Virus mediated genital warts, as well as for use in treatment of non-genital warts, comprising a therapeutically effective amount of compound of Formula 1, optionally in the form of racemic mixtures or enantiomers, or salts or derivatives thereof.

9. Use of a compound of formula 1, wherein substituents X, Y, Z, R¹, R² and R³ have the same meaning as above, optionally in the form of racemic mixtures or enantiomers, or salts or derivatives thereof, as a medicament.

10. Use of a compound of formula 1, wherein substituents X, Y, Z, R¹, R² and R³ have the same meaning as above, optionally in the form of racemic mixtures or enantiomers, or salts or derivatives thereof, in anti-viral cancer treatment in mammals, in treatment of Human Papilloma Virus associated diseases, such as of benign or neoplastic genital Human Papilloma Virus associated diseases, or in treatment of non-genital warts.

11. A method of treating or preventing of cancer or a similar condition in a mammal wherein the p53 pathway is deregulated by viral oncoproteins, comprising administering a therapeutically effective amount of compound of Formula 1, wherein substituents X, Y, Z, R¹, R² and R³ have the same meaning as above, optionally in the form of racemic mixtures or optically pure enantiomers, or their salts or derivatives thereof to said mammal.

12. The method according to embodiment 11, comprising treating or preventing cervical cancer or oropharyngeal cancers.

13. The method according to embodiment 11 or 12, comprising down-regulating oncoproteins and cellular inhibitor of apoptosis protein 2 (c-IAP2).

14. The method according to any of embodiments 11 to 13, comprising reactivating the cell cycle arrest by activating p53-p21 pathway and also inducing p53-independent apoptosis.

15. The method according to any of embodiments 11 to 14, comprising treating Human Papilloma Virus mediated cancer.

16. The method according to any of embodiments 11 to 15, comprising administering compound of Formula 1, wherein substituents X, Y, Z, R¹, R² and R³ have the same meaning as above, or salts or derivatives thereof to the mammal in a dosage of 0.001 mg/kg to about 1000 mg/kg body weight, preferably about 0.1 mg/kg to about 500 mg/kg body weight, in particular 0.001 to 100 mg/kg body weight, advantageously 0.01 to 50 mg/kg body weight per day.

17. A method of treating Human Papilloma Virus associated diseases, such as benign or neoplastic genital Human Papilloma Virus associated diseases, in particular Human Papilloma Virus mediated warts, genital as well as nongenital warts, comprising administering a therapeutically effective amount of compound of Formula 1, wherein substituents X, Y, Z, R¹, R² and R³ have the same meaning as above, optionally in the form of racemic mixtures or optically pure enantiomers, or their salts or derivatives thereof to said mammal.

18. The method according to embodiment 17, comprising topically administering compound of Formula 1, wherein substituents X, Y, Z, R¹, R² and R³ have the same meaning as above, or their salts or derivatives thereof to the mammal.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

INDUSTRIAL APPLICABILITY

As will appear from the foregoing, the present molecules are suitable for preparation of pharmaceutically active compositions for use in anti-cervical cancer and anti-viral treatment in mammals. Further, the present molecules are suitable for use in treatment and prevention of head and neck cancers, in particular HPV-mediated cancers, such as oropharyngeal cancers. The present molecules are also useful as intermediates, precursors and prodrugs for compounds having such activity.

CITATION LIST

Patent Literature
WO2014033366
Non-Patent Literature
1. Bray F, Jemal A, Grey N, Ferlay J, Forman D. Global cancer transitions according to the human development index (2008-2030): a population-based study. *Lancet. Oncol.* 13 (2012) 790-801.

2. American Cancer Society (ACS) 2013. *Cancer facts & figures* 2013.
3. Finzer P, Aguilarlemarroy A, Rosl F. The role of human papillomavirus oncoproteins E6 and E7 in apoptosis. *Cancer Lett.* 188 (2002) 15-24.
4. Marshall J. A., DeHoff B. S. Cembranolide total synthesis. Anisomelic acid. Tetrahedron 43 (1987) 4849-4860.
5. Marshall J. A., DeHoff B S. Stereoselective total synthesis of cembranolide diterpene anisomelic acid, Tetrahedron Lett., 1986, Vol. 27, No. 40, pp. 4873-6.
6. Zeisser-Labouèbe M, Delie F, Lange N. Screening of nanoparticle delivery systems for the photodection of cancer in a simple and cost-effective model. *Nanomedicine* 4 (2009) 135-143.

The invention claimed is:
1. A pharmaceutical composition comprising a therapeutically effective amount of compound of Formula 1,

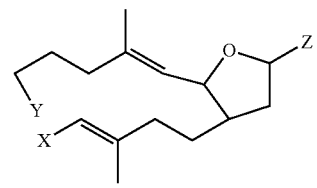

Formula 1 wherein the compound of Formula 1 is selected from the group of:
  5-[(E)-5-[tert-butyl(dimethyl)silyl]oxy-2-methyl-pent-1-enyl]-4-[(3E)-3-methylhexa-3,5-dienyl]tetrahydrofuran-2-ol;
  (E)-6[2-[(E)-5-[tert-butyl(dimethyl)silyl]oxy-2-methyl-pent-1-enyl]-5-methoxy-tetrahydrofuran-3-yl]-4-methyl-hex-3-en-1-ol; and
  (4S,5S)-5-[(E)-5-[(4-methoxyphenyl)methoxy]-2-methyl-pent-1-enyl]-4-[(3E)-3-methylhexa-3,5-dienyl]tetrahydrofuran-2-one and the enantiomer.

2. The pharmaceutical composition according to claim 1, said composition being formulated for administering to a mammal in a dosage of 0.001 mg/kg to about 1000 mg/kg body weight, preferably about 0.1 mg/kg to about 500 mg/kg body weight, in particular 0.001 to 100 mg/kg body weight, advantageously 0.01 to 50 mg/kg body weight per day.

3. A method of treating cancer or a similar condition in a mammal, wherein the p53 pathway is deregulated by viral oncoproteins, comprising administering a therapeutically effective amount of compound of Formula 1

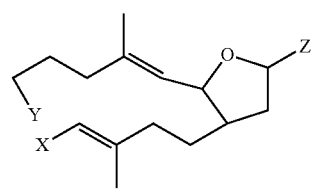

Formula 1 wherein, the compound of formula 1 is selected from the group of:
  5-[(E)-5-[tert-butyl(dimethyl)silyl]oxy-2-methyl-pent-1-enyl]-4-[(3E)-3-methylhexa-3,5-dienyl]tetrahydrofuran-2-ol;

(E)-6[2-[(E)-5-[tert-butyl(dimethyl)silyl]oxy-2-methyl-pent-1-enyl]-5-methoxy-tetrahydrofuran-3-yl]-4-methyl-hex-3-en-1-ol; and (4S,5S)-5-[(E)-5-[(4-methoxyphenyl)methoxy]-2-methyl-pent-1-enyl]-4-[(3E)-3-methylhexa-3,5-dienyl]tetrahydrofuran-2-one and the enantiomer.

4. The method according to claim 3, further comprising treating or preventing cervical cancer or oropharyngeal cancers.

5. The method according to claim 3, further comprising down-regulating oncoproteins and cellular inhibitor of apoptosis protein 2 (c-IAP2).

6. The method according to claim 3, further comprising reactivating the cell cycle arrest by activating p53-p21 pathway and also inducing p53-independent apoptosis.

7. The method according to claim 3, further comprising treating Human Papilloma Virus mediated cancer.

8. The method according to claim 3, further comprising administering compound of Formula 1or salts or derivatives thereof to the mammal in a dosage of 0. 001 mg/kg to about 1000 mg/kg body weight, preferably about 0.1 mg/kg to about 500 mg/kg body weight, in particular 0.001 to 100 mg/kg body weight, advantageously 0.01 to 50 mg/kg body weight per day.

9. A method of treating Human Papilloma Virus associated diseases comprising administering a therapeutically effective amount of compound of Formula 1

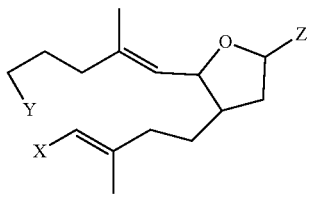

Formula 1 wherein the compound of formula 1 is selected from the group of:

5-[(E)-5-[tert-butyl(dimethyl)silyl]oxy-2-methyl-pent-1-enyl]-4-[(3E)-3-methylhexa-3,5-dienyl]tetrahydrofuran-2-ol;

(E)-6[2-[(E)-5-[tert-butyl(dimethyl)silyl]oxy-2-methyl-pent-1-enyl]-5-methoxy-tetrahydrofuran-3-yl]-4-methyl-hex-3-en-1-ol; and (4S,5S)-5-[(E)-5-[(4-methoxyphenyl)methoxy]-2-methyl-pent-1-enyl]-4-[(3E)-3-methylhexa-3,5-dienyl]tetrahydrofuran-2-one and the enantiomer.

10. The method according to claim 9, further comprising topically administering compound of Formula 1or their salts or derivatives thereof to the mammal.

11. The pharmaceutical composition according to claim 1, wherein the compound of Formula 1 is in the form of a racemic mixture or as optically pure enantiomers, in particular R- or S-enantiomers thereof.

12. The pharmaceutical composition according to claim 1, wherein the compound of Formula 1 is (E)-6[2-[(E)-5-[tert-butyl(dimethyl)silyl]oxy-2-methyl-pent-1-enyl]-5-methoxy-tetrahydrofuran-3-yl]-4-methyl-hex-3-en-1-ol.

13. The method according to claim 3, wherein the compound of Formula 1 is in the form of a racemic mixture or as optically pure enantiomers, in particular R- or S-enantiomers thereof.

14. The method according to claim 3, wherein the compound of Formula 1 is (E)-6-[2-[(E)-5-[tert-butyl(dimethyl)silyl]oxy-2-methyl-pent-1-enyl]-5-methoxy-tetrahydrofuran-3-yl]-4-methyl-hex-3-en-1-ol.

15. The method according to claim 9, wherein the compound of Formula 1 is in the form of a racemic mixture or as optically pure enantiomers, in particular R- or S-enantiomers thereof.

16. The method according to claim 9, wherein the compound of Formula 1 is (E)-6-[2-[(E)-5-[tert-butyl(dimethyl)silyl]oxy-2-methyl-pent-1-enyl]-5-methoxy-tetrahydrofuran-3-yl]-4-methyl-hex-3-en-1-ol.

* * * * *

UNITED STATES PATENT AND TRADEMARK OFFICE
CERTIFICATE OF CORRECTION

PATENT NO. : 10,196,371 B2  
APPLICATION NO. : 15/504696  
DATED : February 5, 2019  
INVENTOR(S) : Rajendran et al.

Page 1 of 1

It is certified that error appears in the above-identified patent and that said Letters Patent is hereby corrected as shown below:

On the Title Page

Item (73) Assignee should read "Åbo Akademi, Åbo (FI)"

Signed and Sealed this  
Twenty-sixth Day of March, 2019

Andrei Iancu  
*Director of the United States Patent and Trademark Office*